(12) United States Patent
Curro et al.

(10) Patent No.: US 6,863,960 B2
(45) Date of Patent: *Mar. 8, 2005

(54) USER-ACTIVATIBLE SUBSTANCE DELIVERY SYSTEM

(75) Inventors: John Joseph Curro, Cincinnati, OH (US); Ali Abdelaziz Alwattari, Hamilton, OH (US); Douglas Herrin Benson, West Harrison, IN (US); Anneke Margaret Kaminiski, Cincinnati, OH (US); Michele Ann Mansfield, Cincinnati, OH (US); John Brian Strube, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 84 days.

This patent is subject to a terminal disclaimer.

(21) Appl. No.: 09/886,893

(22) Filed: Jun. 21, 2001

(65) Prior Publication Data

US 2002/0022427 A1 Feb. 21, 2002

Related U.S. Application Data

(63) Continuation-in-part of application No. 09/467,938, filed on Dec. 21, 1999, and a continuation-in-part of application No. 09/584,676, filed on May 31, 2000, and a continuation-in-part of application No. PCT/US00/34746, filed on Dec. 20, 2000.

(51) Int. Cl.⁷ .............................. B32B 3/00; B32B 3/26; B32B 27/02; B32B 27/14
(52) U.S. Cl. ...................... 428/198; 428/166; 428/172; 428/192; 428/195.1; 428/196; 428/320.2; 428/321.1; 442/392; 442/393; 442/394
(58) Field of Search .............................. 428/195.1, 192, 428/68–76, 195, 196, 198, 320.2, 321.1, 166, 172; 239/34, 53, 55–57; 442/392, 394, 393; 424/449, 443, 402; 604/289, 290

(56) References Cited

U.S. PATENT DOCUMENTS

| 2,257,428 A | 9/1941 | Ruegenberg |
| 2,679,887 A | 6/1954 | Doyle et al. |
| 2,862,251 A | 12/1958 | Kalwaites |
| 2,896,692 A | 7/1959 | Villoresi |
| 3,081,500 A | 3/1963 | Griswold et al. |

(List continued on next page.)

FOREIGN PATENT DOCUMENTS

| EP | 0 112 654 A2 | 7/1984 |
| EP | 0 127 483 B1 | 10/1989 |

(List continued on next page.)

*Primary Examiner*—Cheryl A. Juska
*Assistant Examiner*—Jenna-Leigh Befumo
(74) *Attorney, Agent, or Firm*—Angela Marie Stone

(57) ABSTRACT

A user-activatible substance delivery system of the present invention comprises a first web and a second web, the first and second webs having a periphery and being enclosed about their respective peripheries and defining a void space therein. A substance for delivery upon user activation is disposed in the void space. At least one of the first or second webs has at least one bond site. The bond site(s) define(s) a melt weakened region such that upon application of a force having a vector component parallel to the transverse axis, the bond site(s) fracture(s) to form a corresponding aperture in the respective web. The apertures provide a fluid communication path to facilitate delivery of the substance from the void space.

20 Claims, 10 Drawing Sheets

U.S. PATENT DOCUMENTS

| | | |
|---|---|---|
| 3,081,512 A | 3/1963 | Griswold |
| 3,354,022 A | 11/1967 | Dettre et al. |
| 3,485,706 A | 12/1969 | Evans |
| 3,542,634 A | 11/1970 | Such et al. |
| 3,574,109 A | 4/1971 | Yoshikawa |
| 3,597,299 A | 8/1971 | Thomas et al. |
| 3,681,182 A | 8/1972 | Kalwaites |
| 3,681,183 A | 8/1972 | Kalwaites |
| 3,695,967 A | 10/1972 | Ross |
| 3,695,985 A | 10/1972 | Brock et al. |
| 3,728,203 A | 4/1973 | Taylor |
| 3,800,364 A | 4/1974 | Kalwaites |
| 3,855,046 A | 12/1974 | Hansen et al. |
| 3,860,003 A | 1/1975 | Buell |
| 3,881,987 A | 5/1975 | Benz |
| 3,927,673 A | 12/1975 | Taylor |
| 3,929,135 A | 12/1975 | Thompson |
| 3,949,127 A | 4/1976 | Ostermeier et al. |
| 3,953,638 A | 4/1976 | Kemp |
| 4,062,993 A | 12/1977 | Seward |
| 4,101,625 A | 7/1978 | Haley |
| 4,116,892 A | 9/1978 | Schwarz |
| 4,135,021 A | 1/1979 | Patchell et al. |
| 4,153,664 A | 5/1979 | Sabee |
| 4,207,367 A | 6/1980 | Baker, Jr. |
| 4,223,059 A | 9/1980 | Schwarz |
| 4,276,336 A | 6/1981 | Sabee |
| 4,285,100 A | 8/1981 | Schwarz |
| 4,333,979 A | 6/1982 | Sciaraffa et al. |
| 4,342,314 A | 8/1982 | Radel et al. |
| 4,349,020 A | 9/1982 | Krikorian |
| 4,355,066 A | 10/1982 | Newman |
| 4,404,052 A | 9/1983 | Persson et al. |
| 4,414,970 A | 11/1983 | Berry |
| 4,418,123 A | 11/1983 | Bunnelle et al. |
| 4,421,812 A | 12/1983 | Plant |
| 4,522,863 A | 6/1985 | Keck et al. |
| 4,525,407 A | 6/1985 | Ness |
| 4,573,991 A | 3/1986 | Pieniak et al. |
| 4,588,630 A | 5/1986 | Shimalla |
| 4,600,620 A | 7/1986 | Lloyd et al. |
| 4,603,069 A | 7/1986 | Haq et al. |
| 4,606,964 A | 8/1986 | Wideman |
| 4,609,518 A | 9/1986 | Curro et al. |
| 4,629,643 A | 12/1986 | Curro et al. |
| 4,657,802 A | 4/1987 | Morman |
| 4,695,278 A | 9/1987 | Lawson |
| 4,720,415 A | 1/1988 | Vander Wielen et al. |
| 4,741,944 A | 5/1988 | Jackson et al. |
| 4,758,297 A | 7/1988 | Calligarich |
| 4,797,310 A | 1/1989 | Barby et al. |
| 4,801,482 A | 1/1989 | Goggans et al. |
| 4,808,178 A | 2/1989 | Aziz et al. |
| 4,816,025 A | 3/1989 | Foreman |
| 4,840,829 A | 6/1989 | Suzuki et al. |
| 4,847,134 A | 7/1989 | Fahrenkrug et al. |
| 4,891,258 A | 1/1990 | Fahrenkrug |
| 5,116,662 A | 5/1992 | Morman |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,204,158 A | 4/1993 | Phillips et al. |
| 5,260,345 A | 11/1993 | DesMarais et al. |
| 5,268,224 A | 12/1993 | DesMarais et al. |
| 5,320,891 A | 6/1994 | Levy et al. |
| 5,338,766 A | 8/1994 | Phan et al. |
| 5,376,198 A | 12/1994 | Fahrenkrug et al. |
| 5,431,991 A | 7/1995 | Quantrille et al. |
| 5,451,219 A | 9/1995 | Suzuki et al. |
| 5,518,801 A | 5/1996 | Chappell et al. |
| 5,536,555 A | 7/1996 | Zelazoski et al. |
| 5,567,501 A | 10/1996 | Srinivasan et al. |
| 5,587,225 A | 12/1996 | Griesbach et al. |
| 5,595,567 A | 1/1997 | King et al. |
| 5,620,779 A | 4/1997 | Levy et al. |
| 5,623,888 A | 4/1997 | Zafiroglu |
| 5,626,571 A | 5/1997 | Young et al. |
| 5,628,097 A | 5/1997 | Benson et al. |
| 5,635,290 A | 6/1997 | Stopper et al. |
| 5,658,639 A | 8/1997 | Curro et al. |
| 5,662,634 A | 9/1997 | Yamamoto et al. |
| 5,681,302 A | 10/1997 | Melbye et al. |
| 5,683,374 A | 11/1997 | Yamamoto et al. |
| 5,683,794 A | 11/1997 | Wadsworth et al. |
| 5,691,035 A | 11/1997 | Chappell et al. |
| 5,714,107 A | 2/1998 | Levy et al. |
| 5,733,822 A | 3/1998 | Gessner et al. |
| 5,804,021 A | 9/1998 | Abuto et al. |
| 5,830,555 A | 11/1998 | Srinivasan et al. |
| 5,846,232 A | 12/1998 | Serbiak et al. |
| 5,851,935 A | 12/1998 | Srinivasan et al. |
| 5,853,881 A | 12/1998 | Estey et al. |
| 5,891,544 A | 4/1999 | Chappell et al. |
| 5,906,879 A | 5/1999 | Huntoon et al. |
| 5,916,661 A | 6/1999 | Benson et al. |
| 5,919,411 A | 7/1999 | Rezai et al. |
| 6,015,605 A | 1/2000 | Tsujiyama et al. |
| 6,022,607 A | 2/2000 | James et al. |
| 6,025,050 A | 2/2000 | Srinivasan et al. |
| 6,027,593 A | 2/2000 | Lunt et al. |
| 6,054,202 A | 4/2000 | Takeuchi et al. |
| 6,057,024 A | 5/2000 | Mleziva et al. |
| 6,086,984 A | 7/2000 | DiMaggio, Jr. et al. |
| 6,106,925 A | 8/2000 | Palumbo |
| 6,203,654 B1 | 3/2001 | McFall et al. |
| 6,537,930 B1 * | 3/2003 | Middlesworth et al. ........ 442/39 |

FOREIGN PATENT DOCUMENTS

| | | |
|---|---|---|
| EP | 0 164 740 B1 | 4/1990 |
| EP | 0 432 755 B1 | 5/1995 |
| EP | 0 432 763 B1 | 8/1995 |
| EP | 0 685 586 A2 | 12/1995 |
| EP | 0 687 757 A2 | 12/1995 |
| EP | 0 452 727 B1 | 3/1996 |
| EP | 0 758 543 A1 | 2/1997 |
| EP | 0 713 546 B1 | 3/1997 |
| EP | 0 677 284 B1 | 6/1999 |
| EP | 0 919 212 A2 | 6/1999 |
| EP | 0 945 251 A1 | 9/1999 |
| EP | 0 945 536 A2 | 9/1999 |
| EP | 0 955 159 A1 | 11/1999 |
| EP | 0 823 878 B1 | 8/2000 |
| JP | 08299385 A | 11/1996 |
| WO | WO 94/19179 A1 | 9/1994 |
| WO | WO 96/10979 A1 | 4/1996 |
| WO | WO 97/11662 A1 | 4/1997 |
| WO | WO 97/47264 A1 | 12/1997 |
| WO | WO 99/37476 A1 | 7/1999 |
| WO | WO 99/55273 A1 | 11/1999 |
| WO | WO 99/55532 A1 | 11/1999 |
| WO | WO 99/67081 | 12/1999 |
| WO | WO 00/76430 A1 | 12/2000 |
| WO | WO 01/45616 A1 | 6/2001 |

* cited by examiner

USER-ACTIVATIBLE SUBSTANCE DELIVERY SYSTEM

CROSS REFERENCE TO RELATED APPLICATION

This application is: a continuation-in-part and claims priority of prior application PCT International Application Ser. No. US00/34746 (Case 7897R2) which designates the US, will publish in English, and was filed Dec. 20, 2000 in the names of Curro et al.; and a continuation-in-part and claims priority of prior application Ser. No. 09/584,676 (Case 7897R2), filed May 31, 2000 in the names of Curro et al.; and a continuation-in-part and claims priority of prior application Ser. No. 09/467,938 (Case 7897), filed Dec. 21, 1999 in the names of Curro et al.

FIELD OF THE INVENTION

This invention relates to user-activatible substance delivery systems, and in particular such systems that can be activated by stretching.

BACKGROUND OF THE INVENTION

Packaged soaps, fragrances, lotions, adhesives, and the like are well known in the art. Such substances are typically delivered in disposable packaging. For example, hand soap can be provided in an appropriate package such as a folded wrapper that the user removes prior to use. Liquids such as shampoo and lotion are commonly supplied in a tear-open packet, and dispensed for use directly from the packet. Likewise, liquids such as lotion, soap, fragrance and the like can be supplied on a substrate such as a wipe contained in a sealed package. The user can open the package, such as by tearing, remove the wipe, and transfer the liquid onto the skin, for example.

In many known substance delivery systems and packages, therefore, the substance to be delivered is removed from the packaging, and the packaging is then discarded. That is, the packaging serves little purpose beyond simply protecting the substance prior to use by the consumer. Such a practice is wasteful, as after the point of sale the packaging merely becomes trash that must be dealt with accordingly.

Accordingly, it would be desirable to have a substance delivery system that effectively utilizes its own packaging so that the packaging does not necessarily get thrown away before use of the substance.

Additionally, it would be desirable to have a substance delivery system that can be activated by the user with minimal effort.

Finally, it would be desirable to have a substance delivery system in which the packaging is useful for other purposes by the consumer.

BRIEF SUMMARY OF THE INVENTION

A user-activatible substance delivery system of the present invention comprises a first web and a second web, the first and second webs having a periphery and being enclosed about their respective peripheries and defining a void space therein. A substance is disposed in the void space. At least one of the first or second webs has at least one bond site, the bond site having a longitudinal axis oriented in a first direction and a transverse axis oriented in a second direction orthogonal to the first direction. The (or each) bond site(s) define(s) a melt weakened region such that upon application of a force having a vector component parallel to the transverse axis, the bond site(s) fracture(s) to form a corresponding aperture in the respective web. The apertures provide a fluid communication path to facilitate exposure or delivery of the substance.

In another embodiment, a user-activatible substance delivery system of the present invention comprises a first web and a second web joined in a face-to-face relationship at a plurality of discrete bond sites, each bond site having a longitudinal axis oriented in a first direction and a transverse axis oriented in a second direction orthogonal to the first direction. A substance for delivery upon user activation is disposed in an interior region between the first and second webs. Each bond sites defines a melt weakened region such that upon application of a force having a vector component parallel to the transverse axis, the bond sites fracture to form a corresponding aperture in the respective web. The apertures have unbonded portions about their respective peripheries, which thereby provide a fluid communication path to facilitate exposure or delivery of the substance.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
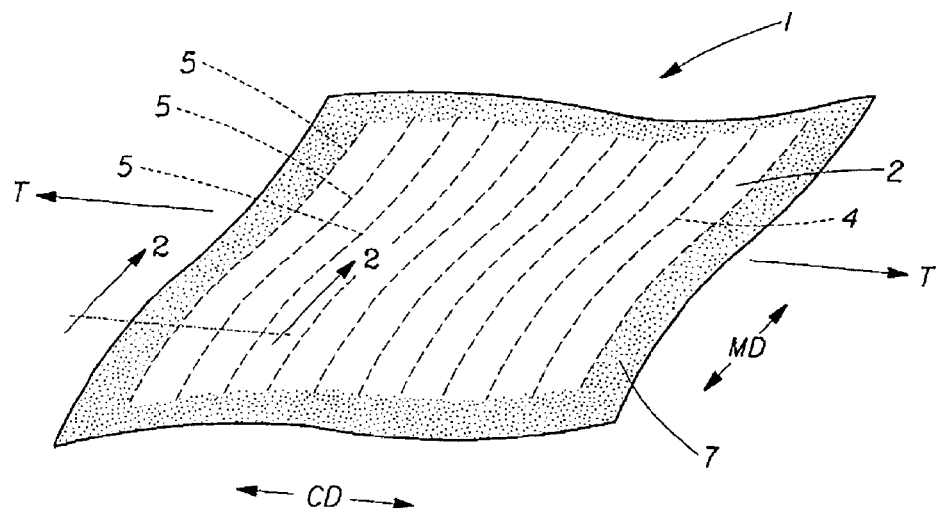
FIG. 1 is a perspective view of one embodiment of a user-activatible substance delivery system of the present invention.

As used herein, the term "user-activatible" is used to describe articles that are delivered to the user in one state, and intended to be altered by the user, such as by stretching, to be in another state suitable for, and capable of, performing a useful function, such as exposure or delivery of a beneficial substance.

As used herein, the term "substance delivery system" is used to describe a combination of a substance, such as a liquid, gas, powder, or the like, and a package for containing the substance, the combination being suitable for use by a consumer who can "activate" the system, as described herein, to facilitate exposure or delivery of the substance.

Thus, a user-activatible substance delivery system comprises a substance contained in a package, considered together herein as a system, until such time that the user activates (or causes activation of the system, thereby facilitating delivery or exposure of a substance for its intended use. A non-limiting example of a substance delivery system of the present invention is a sealed packet, or pouch, having contained therein a liquid substance such as perfume, antibacterial lotion, sunscreen, or the like, the liquid substance being contained until the user activates the system by applying a tensioning force in a specified direction, at which time the liquid substance can be released from the packet. Therefore, a particular benefit of the present invention is that the substance delivery systems are user-activatible with minimal effort, and, as described hereinbelow, the container, or packaging, need not necessarily get thrown away before use of the substance but can be useful for other purposes.

As used herein, the term "film" or "polymer film" is used to describe liquid impervious polymer films as are known in the art. Such films are typically thin films supplied as webs. Typical materials for such films include, without limitation, polyethylene, polypropylene, polyester, cross-linked polymers, and combinations thereof. Such films can be rendered liquid pervious by known methods such as aperturing. Such films can also be microporous and/or "breathable" to permit gas and vapors to penetrate, while remaining essentially liquid pervious. Such films may be made microporous before user activation or may consist of precursor (filled) films which become microporous upon user activation. As used herein, the term "nonwoven web" is used in its plain meaning as understood in the art and refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers" refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers" refers to small diameter fibers that are formed by extruding a molten thermoplastic material as filaments from a plurality of fine, usually circular, capillaries of a spinneret with the diameter of the extruded filaments then being rapidly reduced by drawing.

As used herein, the term "unitary web" refers to a laminate of two or more webs of material, including polymer films and nonwoven webs, that are sufficiently joined, such as by thermal bonding means, to be handled, processed, or otherwise utilized, as a single web.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches.

Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are denoted herein by the term "highly elastic" which refers to any material which upon application of a biasing force, is stretchable, that is, elongatable, at least about 200 percent (i.e., to a stretched, biased length, which is at least about 300 percent of its relaxed unbiased length), and which, will to within 105 percent of their initial relaxed length, upon release of the stretch force. Therefore, highly elastic materials are generally also elastic, but not all elastic materials are highly elastic.

As used herein, the term "nonelastic" refers to any material that does not fall within the definition of "elastic" above.

As used herein, the term "extensible" refers to any material that, upon application of a biasing force, is elongatable, at least about 25 percent without experiencing catastrophic failure. Catastrophic failure includes substantial tearing, fracturing, rupturing, or other failure in tension such that, if tested in a standard tensile tester, the failure would result in a sudden significant reduction in tensile force. As used herein, the term "highly extensible" refers to any material that, upon application of a biasing force, is elongatable, at least about 100 percent without experiencing catastrophic failure.

As used herein, the term "fluid" refers to both liquids and gases. Liquids include both relatively low viscosity fluids (i.e., less than about 5,000 cps) and relatively high viscosity fluids (i.e., greater than about 5,000 cps).

As used herein, the term "machine direction" is used as is commonly known in the art, and refers to the longitudinal direction of a web material being processed. "Cross-direction" is likewise used as is commonly known in the art, and refers to a direction orthogonal and in the same plane as the machine direction. In a finished article made from such webs, the terms machine direction and cross-direction refer to the respective directions of the precursor web, prior to forming into the finished article.

Figure 2:
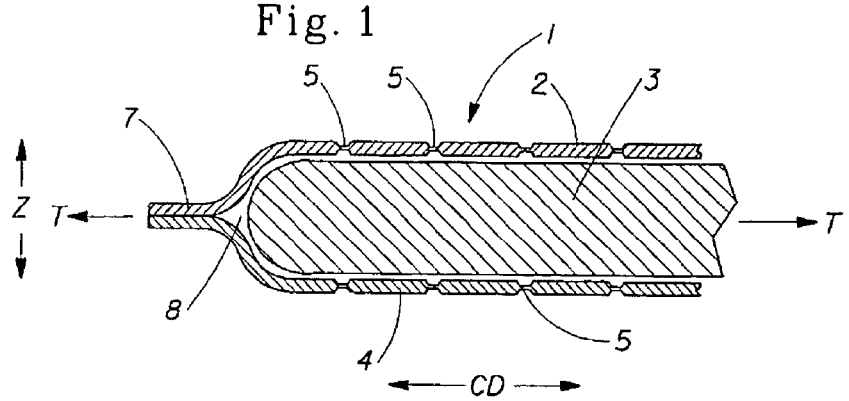
FIG. 2 is a cross-sectional view of a portion of the user-activatible substance delivery system shown in FIG. 1.

One embodiment of a user-activatible substance delivery system of the present invention is shown in FIGS. 1 and 2. As shown, substance delivery system 1 comprises a substance 3 contained in a package that can be described in this embodiment as a pouch formed of a first web, called first outer layer 2, and a second web, called second outer layer 4. Outer layers 2 and 4 have peripheral edges, referred to as peripheries, which are joined to form a peripheral edge 7. In some embodiments, the extensibility of the peripheral edge can be preserved by the use of extensible or elastic adhesives or by intermittent closely spaced thermal bonds. Outer layers can be sealed about peripheral edge 7 by any suitable method such as by adhesive bonding. If outer layers 2 and 4 are thermoplastic materials, suitable methods can include continuous or intermittent heat sealing, for example.

The pouch of the embodiment shown in FIGS. 1 and 2 can be formed by two separate webs joined about their entire respective peripheries. The pouch can also be formed in other known ways, such as by folding a single web onto itself (e.g., a C-fold, sometimes referred to as a wallet-fold) and sealing about the unjoined peripheral edges (e.g., three unjoined edges if the pouch is rectangular in shape, two unjoined edges if the pouch is triangular in shape, etc.). If the pouch is formed by folding a single web upon itself, the two respective "legs" of the fold, e.g., the two panels formed by the folding, can be considered as the first and second webs, that is, the outer layers 2 and 4 as described herein.

By joining the first and second webs about their respective peripheries, a void space 8 is defined between the first and second layers 2 and 4. It is in this void space that the substance 3 to be delivered is disposed.

One or both outer layers 2 or 4, can be a thermoplastic material, such as a film or a nonwoven material, or a woven fabric. If the substance delivery system in the form of a pouch as shown in FIG. 1 is to be hermetically sealed, then outer layers 2 and 4 should comprise a liquid impervious film layer, such as common packaging materials known in the art. Suitable films include P18-2870 and P18-1401 having a thickness generally in the range of from about 0.5 to about 10 mils, and available commercially from Clopay, Inc. located in Cincinnati, Ohio. Film layers of this type can have basis weights in the range of from about 10 grams per square meter (gsm) to about 250 gsm.

In certain embodiments, such as delivery of dry soap, e.g., powdered soap, to be wetted by the user upon activation of the substance delivery system, or for delivery of highly viscous materials, one or both outer layers 2 or 4 can be relatively porous materials, such as nonwoven materials. Any thermofusable nonwoven material may be used for the present invention, including spunbonded, meltblown, carded, and spunlaced materials. The term thermofusable, as used herein, refers to materials which when subjected to sufficient heat and/or pressure will form a bond site. In general, all thermoplastic materials are thermofusable. In preferred embodiments, the nonwoven material can have a basis weight between 10 and 100 gsm. The particular type of nonwoven can be chosen for selected properties, such as softness, abrasiveness, cost, availability, and other technical, market or commercial considerations. Certain preferred nonwoven materials are disclosed more fully herein below with respect to additional embodiments.

Figure 3:
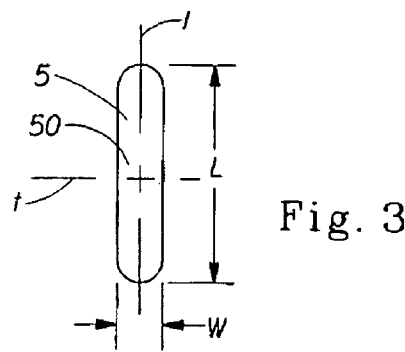
FIG. 3 is a magnified detail view of one bond site of a user-activatible substance delivery system of the present invention.

One or both outer webs 2 or 4 of the substance delivery system 1 shown in FIG. 1 have a plurality of bond sites 5 that serve to weaken the web in the immediate vicinity of the bond site 5. The term "bond site" in the context of embodiments such as that shown in FIG. 1 refers to a localized region of the web made weak by application of heat and pressure, and may or may not refer to the joining of more than one layer. Therefore, bond sites 5 can be described as melt weakened regions in a single layer or in a laminate of multiple layers. One representative bond site is shown in FIG. 3. As shown, bond site 5 has an elongated shape, with a longitudinal axis l, which corresponds directionally to the length dimension, L, of bond site 5, and a transverse axis t, which is perpendicular to longitudinal axis l, and corresponds directionally to the width dimension, W of bond site 5. For non-limiting descriptive purposes, the bond site 5 can be considered to be two-dimensional, with the axes l and t defining a plane of the bond site 5.

In one embodiment, each bond site 5, is disposed in a plurality of bond sites 5 in a regular, repeating pattern with the longitudinal axes l of each bond site 5 oriented in the same direction, for example, in the machine direction, MD of the outer layer 2 and/or 4, as shown in FIG. 1. But the longitudinal axes of each bond site may be disposed in a regular, repeating pattern oriented in the cross machine direction, or pseudo-randomly oriented in a mixture of cross and machine directions. In one embodiment, at least a portion of the total number of bond sites comprises bond sites having their respective longitudinal axes l oriented in the same direction. For example, the bond sites 5 can be disposed in a "herringbone" pattern, in which a first portion of bond sites 5 have their respective longitudinal axes l oriented in a first direction, and a second portion of bond sites 5 have their respective longitudinal axes l oriented in a second direction, which is disposed at an angle to the first direction.

Each bond site 5 forms localized melt weakened portions of the respective web layer 2 and/or 4 in the region of the bond site such that upon application of a force having a vector component parallel to the respective transverse axis t, sufficient to cause the bond site 5 to fracture, or tear, or otherwise fail in tension, a an aperture, or opening, is formed in substance delivery system 1. The vector component of the applied force must be sufficient to fracture the melt weakened region of bond site 5, and, therefore, the force required can be minimized, for a given combination of webs and substances, but applying the force wholly parallel to transverse axis t. In one embodiment, this is accomplished by a user grasping a substance delivery system of the present invention along the appropriate opposing edges and pulling, such that the system can be considered to be a two-dimensional system, with substantially all the forces applied in a direction corresponding to the transverse axis t of a respective bond site. In another embodiment, the applied force can be generated by a usage regimen in which the user initiates a process which indirectly applies sufficient tensioning forces. Therefore, with respect to vector components of applied forces, the term "parallel to the transverse axis" is meant to distinguish forces that may be applied, for example, in what is denoted as the "Z" direction in FIG. 2. The relatively high aspect ratio of melt bond sites 50, permits relatively large apertures to be formed upon sufficient extension.

Figure 4:
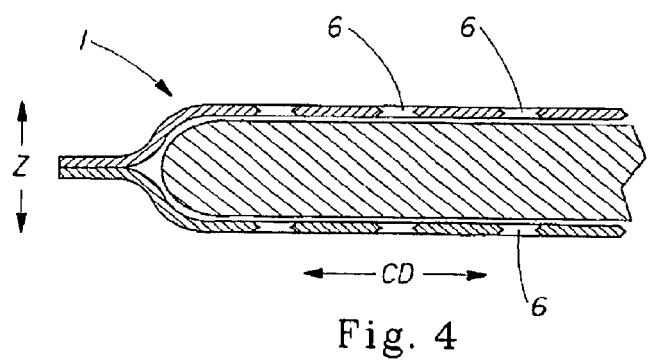
FIG. 4 is a cross-sectional view of a portion of the laminate web shown in FIG. 1 after user activation.

With reference to FIGS. 1 and 2, if at least one bond site 5 is oriented with its respective longitudinal axes l aligned in the machine direction MD, and tension is applied in the direction T corresponding to the cross-direction CD, the tensile force applied at the bond site 5 will cause the bond site to rupture, open and spread, forming an aperture, or opening 6 as shown in cross section in FIG. 4. In general, for a plurality of bond sites 5, when the substance delivery system 1 is uniformly tensioned, the result is a regular pattern of a plurality of apertures 6 corresponding to the pattern of melt bond sites 5. In certain embodiments, the requisite force application can be applied by a user by simply grasping the substance delivery system 1 by the appropriate edges and pulling with sufficient force to effect fracture and opening of the bond site(s) 5.

It is important to distinguish bond sites 5 from other, known "lines of weakness", such as lines formed by a series of closely spaced perforations. Bond sites 5 are not perforations, and, as such, do not provide for fluid communication between void space 8 and the outside of the system 1, until activation by the user, as described above.

Therefore, in one embodiment a user-activatible substance delivery system, as shown in FIG. 1, is achieved by providing a sealed pouch (either hermetically sealed or relatively porous webs sufficiently dense to contain a substance) that can be stretched by the user, or consumer, to form apertures that serve to enable release of a packaged substance inside. For example, outer layers 2 and 4 can be fluid impervious films formed into a hermetically sealed pouch containing a substance 3, such as a cleansing fluid. The substance delivery system 1 remains dry until the user applies a tensioning force T in the appropriate direction, at which time the apertures 6 are formed, and the contained substance 3 can be released. Particular tensioning forces can be determined by such technical factors as appropriate material selection and bond site dimensions such that sufficient tension can easily be accomplished by hand, for example by grasping opposing sides of the pouch and pulling in the appropriate direction.

In another embodiment a user-activatible substance delivery system, as shown in FIG. 1, is achieved by providing a sealed pouch (either hermetically sealed, or relatively porous webs sufficiently sealed about edges to contain a substance) in which a user initiates a usage regimen wherein the sufficient vector component forces as described above are generated indirectly. An example of such a usage regimen is a detergent release packet where once placed in the washing machine by the user is activated by the mechanical activation of the washing machine.

Many other variations of the present invention as shown in FIG. 1 can be achieved. For example, outer layers 2 and/or 4 can comprise nonwoven webs such as a nonwoven/film laminate, and the substance 3 can be a dry soap powder. The user can conveniently carry the pouch, for example, in his or her pocket. When stretched in the appropriate direction, outer layers 2 and/or 4 become apertured as described above, and, when wetted, the dry soap can lather. Thus, a washcloth is provided by the combination of a soft, pliable nonwoven and the cleanser that is exposed upon stretching. In this manner, the washcloth can be conveniently carried in one's pocket or purse, for example, until use. When desired, the user simply activates the packaging by stretching, at which time the package becomes the washcloth portion.

Another variation of the embodiment shown in FIG. 1 is that each layer 2 or 4 can be a laminate, for example a laminate web comprising a film/metal foil and a nonwoven material. In one embodiment, the laminate is packaged into a pouch having the nonwoven layer exposed to the outside. In this manner, a volatile and/or chemically reactive substance, for example, can be hermetically packaged in the pouch. Once tensioned and apertured, as described above, the enclosed substance can be exposed.

The substance 3 enclosed in the pouch of the embodiment disclosed with reference to FIG. 1 could be any substance that is useful for consumer-activatible substance delivery systems. For example, the substance 3 can be a low viscosity fluid, such as a perfume, which can be exposed upon activation and then wiped onto the body using a nonwoven outer layer 2 or 4. Other relatively low viscosity fluids include water, and compositions having a similar viscosity as water, such as water-based cleaning fluids. Likewise, substance 3 can be a relatively high viscosity fluid such as an oil, a grease, a cream, a gel, or a lotion, such as a sunscreen lotion, an insect repellent lotion, a skin softening lotion, and the like. Substance 3 could also be a teething gel. The teething gel would be contained within a pouch on a disposable bib. The disposable bib could be worn by an infant who bites on the teething gel releasing it onto the infant's gums.

For medical purposes, substance 3 can be a sterile substance, such as an antibacterial cream, which can be exposed by the stretching described above, and applied by wiping. In another use, the entire pouch can be a bandage, suitable for user activation to expose a medicinal substance 3 and applied directly on a wound, for example.

In another embodiment, the substance 3 can be an adhesive substance. Adhesives can comprise high viscosity fluid adhesive substances. A preferred adhesive substance is one that remains tacky over time, such as H-2120 or H-2511. Suitable adhesives include hot melt adhesives, such as H-2031 available form Ato-Findley, Wauwatosa, Wis., which can be applied by spraying, slot coating and other means known in the art. The pouch can be configured to be used as an adhesive attachment means. In this embodiment, the outer layers 2 or 4 can be a film, for example, which are activated by stretching to expose an adhesive substance 3 inside. The film can then be applied as an adhesive tape, for example. In this embodiment, it may be beneficial to provide the "pouch" as a tape, or a web in a roll-wound configuration, as is known in the art for adhesive tapes. In this embodiment, only the longitudinal edges would be sealed as edges 7 in FIG. 1. In a preferred configuration, the direction of tension T would be in the longitudinal direction of the tape, such that by pulling the ends of a tape length, user activation is achieved.

In another embodiment adhesive substance 3 can be 3M spray adhesive applied by spraying, silicone adhesives such as RTV adhesive applied by extrusion, and hot melt adhesives that are not tacky at room temperature, but which can be re-tackified at elevated temperatures and/or pressures.

In another embodiment, the substance 3 is a body adhesive, possibly in combination with a medicinal substance, such that the substance delivery system 1 can be a self-sticking adhesive bandage. Such a bandage can be applied tightly by wrapping around a body part, with the user-activated exposure of the substance 3 being achieved during the wrapping process.

In another embodiment, layers 2 and/or 4 can be materials having recoverable and/or elastomeric properties such that any apertures are recloseable to discontinue or significantly limit the exposure of the substance 3. For example, in the adhesive bandage described above, upon removal of the applied force that formed the apertures, the apertures substantially reclose preventing further exposure of the adhesive until a subsequent application of force is applied. In this manner, a bandage similar to an "ace bandage" can have an inherent retention means, and can be reused a number of times.

Alternately, substance 3 could be metered over a period of time by sequentially releasing a portion of substance 3. For example, if substance 3 is a sunscreen, a portion of the sunscreen could be applied upon a first activation with additional portions applied as needed at a later time.

Other combinations of outer layer materials and substances 3 can be achieved in like manner as described above. Without being bound by theory, it is believed that any substance containable by suitable outer layers formed into the pouch as described above, can be packaged in a system of the present invention. The possible combinations are limited only by the range of useful applications of such a substance delivery system.

The bond sites 5 are melt weakened locations formed by a thermal point calendaring process described below with respect to additional embodiments of the system of the present invention. That is, the process described below with respect to FIG. 9 can be used to form each of layers 2 and/or 4, including laminate materials.

The bond sites 5 have a relatively narrow width W dimension and a relatively high aspect ratio. For example, FIG. 3 shows a schematically a representative melt area of a single melt bond site 5 having a narrow width dimension W and a high aspect ratio, i.e., the length, L, is much greater than the width, W. Width W can be between about 0.003 inches and 0.020 inches, but in a preferred embodiment, is between about 0.005 inches and 0.010 inches, and may be adjusted depending on the properties desired. The dimensions of individual bond sites 5 and their relationship to adjacent bond sites (i.e., the bond pattern) are determined by the pattern of protuberances used in the bonding apparatus. While in a one embodiment, as shown in FIG. 1, the pattern comprises a plurality of bond sites 5 each having their respective longitudinal axes l oriented in the same direction, in some embodiments it may be desirable to have the axes l oriented in varying directions, or randomly. In any event, the mechanism of activation to form an aperture 6 at any given bond site 5 works most effectively when tension is applied in a direction having a vector component in a direction parallel to the axis t.

It is believed that the aspect ratio of bond site 5 can be as low as about 2 (i.e., aspect ratio of L/W equals 2/1) and still permit adequate low tension extension of the web in the appropriate direction, to effect the transition of the bond sites into apertures. The aspect ratio can also be between about 2 and 100 or between about 3 and 50 or preferably between about 4 and 30. In one embodiment, the aspect ratio was about 10 and in other embodiment about 25. The aspect ratio of the bond sites 5 is limited only by the corresponding aspect ratio of the point bonding protuberances of the calendaring roller(s) which form bond sites 5, as detailed below.

When nonwoven webs are used as outer layers 2 or 4 of substance delivery system 1, an important distinction should be drawn between bond sites 5, and thermal bond sites that may be present in the constituent layers themselves. For example, nonwoven webs are typically consolidated by thermal bonding in a regular pattern of discrete spaced apart fused bonding areas, such as the pattern disclosed in U.S. Pat. No. 3,855,046 to Hansen et al., and the patterns shown generally in FIGS. 10 and 11 of U.S. Pat. No. 5,620,779 to Levy et al. Other films, nonwoven webs, and the like may have thermal embossments for aesthetic reasons. Bond sites 5 are distinguished primarily by their relatively high aspect ratio, and their propensity to weaken the respective web appropriately to effect fracture upon tension, causing the bond site 5 to become aperture 6. The bond sites of commercially-available nonwoven webs, for example, do not typically have an aspect ratio greater than 1, and, therefore, do not have a longitudinal dimension. Together the bond sites of the base nonwoven and bond sites 5 define a complex pattern of bond sites that may or may not be described as columnar, regular, or uniform.

Figure 5:
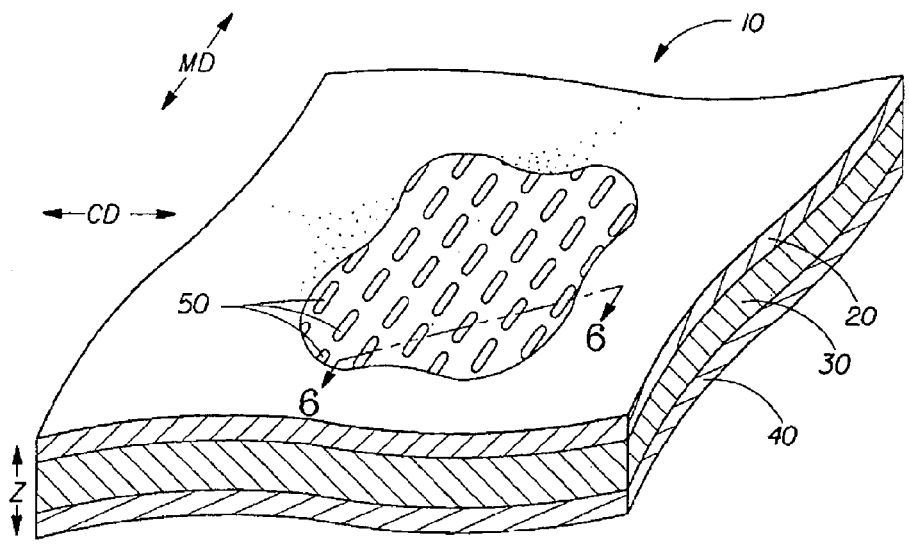
FIG. 5 is a perspective view of another embodiment of a user-activatible substance delivery system of the present invention.
Figure 6:
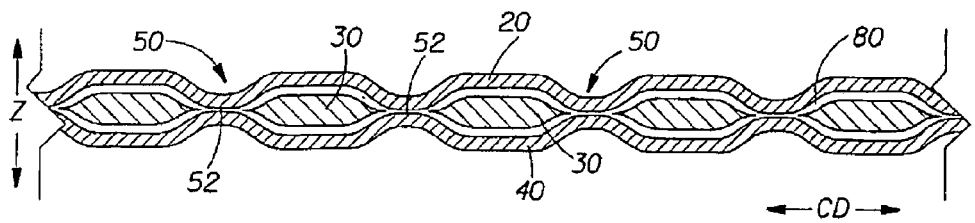
FIG. 6 is a cross-sectional view of a portion of the user-activatible substance delivery system shown in FIG. 5.

Another embodiment of a substance delivery system of the present invention is shown as substance delivery system 10 in FIG. 5. FIG. 5 shows a partially cut away portion of a substance delivery system, at least a portion of which is a bonded laminate in which a first outer layer 20 and a second outer layer 30 are bonded to one another by a plurality of bond sites 50 in a face-to-face relationship, as shown in FIGS. 5 and 6.

The layers 20 and 30 should be sufficiently thin to be processible as described herein, but no actual thickness (i.e., caliper, that is, dimension in the Z-direction) is considered limiting. First outer layer 20 is preferably thermofusable, and is preferably a thermoplastic film or a nonwoven web comprising a sufficient quantity of thermofusable material to effect thermal bonding at bond sites 50. By "sufficient quantity" is meant a quantity of thermofusable material adequate to enable enough thermal bonding upon application of heat and/or pressure to produce a unitary laminate web. A second outer layer, 40, is preferably the same material as first outer layer 20, but may be a different material, also being thermally bondable. Substance 30 is disposed between the two outer layers.

The bond sites 50 are formed by joining means, such as by ultrasonic welding, or thermal calendaring as described below, that serve to couple the outer layers 20 and 40, and, in some embodiments, portions of substance 30, together, thereby forming the constituent components into a unitary web. When joined together, the two outer layers form an interior region 80 between them. The interior region is the space between the outer layers surrounding the bond sites 50. In a preferred embodiment, the substance 30 substantially fills the interior region.

While the substance delivery system 10 is disclosed primarily in the context of nonwoven webs and composites, in principle the substance delivery system 10 can be made out of any web materials that meet the requirements, (e.g., melt properties, relatively low caliper) to be processed by the method disclosed herein. For example, the outer layers 20 and 40 can be films, micro-porous films, apertured films, and the like. Substance 30 can be any substance capable of being delivered for use when the substance delivery system 10 is user-activated by stretching.

If substance 30 is itself supplied as a web material of some type, or applied on a web material, it is apertured during processing into the substance delivery system 10. Thus, in the embodiment shown in FIG. 5, a three-layer laminate substance delivery system 10 is characterized by the substance delivery system 10 (as a whole) being un-apertured prior to use, while the web material comprising substance 30 is apertured. One way of describing substance delivery system 10, is that when viewed orthogonally by the un-aided human eye from a distance of approximately 50 cm, it exhibits no apertures or perforations through the entire laminate, but bond sites 50 are nevertheless visible.

The substance delivery system 10 is further characterized in that the joining of the outer layers 20 and 40 into a unitary article can be achieved in the absence of adhesive. That is, while adhesive can be used in certain embodiments, in certain preferred embodiments no adhesive is required to bond the layers 20 and 40 together; joining is achieved by the input of energy into the constituent layers, such as by thermal melt bonding of the two outer layers together at the bond sites 50. In other embodiments, the energy input can be via ultrasonic bonding. Accordingly, a significant benefit of the present invention is the provision of a substance delivery system in the form of a unitary web, formed without the use of adhesives.

As shown in FIG. 6, substance 30 is chosen such that when the constituent web layers 20 and 40 of substance delivery system 10 are joined at bond sites 50, portions of substance 30 in the region of the bond sites 50 separate to permit the first outer layer 20 to melt bond directly to the second outer layer 40 at the interface of the two materials 52 at bond sites 50. Thus, substance 30, if uniformly distributed between layers 20 and 40, is substantially displaced just prior to the bonding of the outer layers as detailed by the method of the present invention below.

Substance 30 need not be thermally compatible with outer layers 20 and 40. Substance 30 need not be a thermoplastic material, and need not even have a melting point. It simply needs to be displaceable by the forces exerted by the processing apparatus as detailed below. It is also important to consider that, if thermal bonding is used as the bonding technique, substance 30 should have suitable volatility characteristics so as not to combust during processing.

Another advantage of the method of the present invention is that, in some embodiments, e.g., for liquid substance 30 or for solid core substance 30 materials (i.e., a substance 30 delivered as, or on, a continuous sheet, that is, not having substantial apertures, gaps, or other voids), it results in a substance 30 in full, intimate contact with the outer layers 20, and 40. By "full" and "intimate" is meant that substance 30 fills all the unbonded regions between outer layers 20 and 40 such that outer layers 20 and 40 do not contact except at the bond sites 50. Of course, it is recognized that many substance of interest can have significant air content, and filling "all" the unbonded region between outer layers 20 and 40 is not meant to imply that all air content is removed. This may be desired to improve stability of the substance 30 prior to use.

Substance delivery system 10 is formed by the thermal point calendaring process described below. As with the embodiment described with reference to FIGS. 1–3, the bond sites 50 have a narrow width W dimension and a high aspect ratio. For example, with reference again to FIG. 3, the melt area of a single bond site 50 has a narrow width dimension W and a high aspect ratio, i.e., the length, L, is much greater than the width, W. The length L should be selected to permit adequate bond area while width W is sufficiently narrow such that the protuberance used to form the bond site (as described below) can cut, shear, displace, or otherwise negotiate the substance 30 at the region of the bond sites by the method described below. Width W can be between about 0.003 inches and 0.020 inches, but in a preferred embodiment, is between about 0.005 inches and 0.010 inches, and may be adjusted depending on the properties of substance 30.

It is believed that the aspect ratio of melt bond site 50 can be as low as about 2 (i.e., ratio of L/W equals 2/1). The aspect ratio of the bond sites 50 is limited only by the corresponding aspect ratio of the point bonding protuberances of the calendaring roller(s), as detailed below.

In one embodiment, each bond site 50, is disposed in a plurality of bond sites 50 in a regular, repeating pattern with the longitudinal axes 1 of each bond site 50 oriented in the same direction, for example, in the machine direction, MD of the outer layer 20 or 40, as shown in FIG. 5. In one embodiment, at least a portion of the total number of bond sites comprises bond sites having their respective longitudinal axes 1 oriented in the same direction. For example, the bond sites 50 can be disposed in a "herringbone" pattern, in which a first portion of bond sites 50 have their respective longitudinal axes 1 oriented in a first direction, and a second portion of bond sites 50 have their respective longitudinal axes 1 oriented in a second direction, which is disposed at an angle to the first direction.

Figure 17:
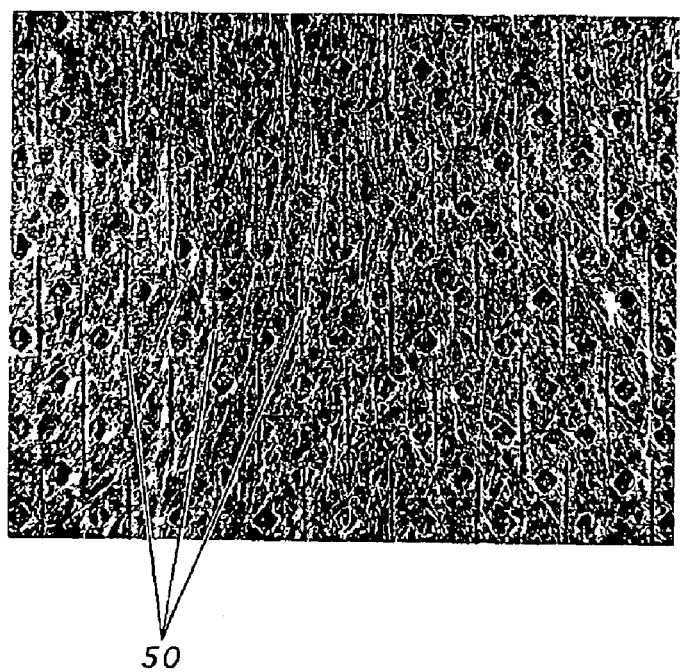
FIG. 17 is a photograph showing a representative nonwoven web having consolidation bonds and high aspect ratio bond sites.

When nonwoven webs are used as constituent layers of substance delivery system 10, an important distinction should be drawn between bond sites 50 that bond together outer layers 20 and 40 by the method of the present invention, and thermal bond sites that may be present in the constituent layers themselves. As mentioned above, nonwoven webs are typically consolidated by thermal bonding in a regular pattern of discrete spaced apart fused bonding areas. Other films, nonwoven webs, and the like may have thermal embossments for aesthetic reasons. Therefore, in the substance delivery system 10 there may be many thermal bond sites, some of which are bond sites 50, and others which are bond sites in the base nonwoven, for example. Bond sites 50 can be distinguished in the embodiment shown generally in FIGS. 5–6 not only by their relatively high aspect ratio, but in that they bond outer layers 20 and 40 together. This distinction can clearly be seen in the photograph of FIG. 17 showing a representative nonwoven web having diamond-shaped consolidation bonds and high aspect ratio bond sites 50.

The resulting system of the present invention, as shown in cross-section in FIG. 6, is a substance delivery system 10 that is itself unapertured, but the substance 30 is apertured coincident the regions of the bond sites 50. Of course, if substance 30 is a viscous substance, or a liquid, the term "apertured" simply refers to the fact that if the viscous or liquid substance was to be made solid, such as by freezing, the substance 30 would exhibit apertures. As stated above, by "unapertured" is meant that, on the whole, the substance delivery system 10 is considered unapertured.

It is recognized that the un-apertured substance delivery system 10 of the present invention may have localized cut through, or tearing at bond sites 50 due to materials and processing variability or post lamination handling. For commercial reasons, such cut through of the entire web should be eliminated, and for hermetically-sealed embodiments, it must be eliminated. Likewise, it is recognized that in some instances, there may not be complete displacement of the substance 30 at all locations of bond sites 50 such that some localized portions of substance 30 may not be completely displaced (and the outer layers not bonded). Nevertheless, the description herein is made for the substance delivery system 10 as a whole, and is not meant to be limited by aberrations or anomalies due to potential material or processing variables.

The substance 30 itself need not be thermally compatible with the outer layers. The substance 30 need not even be melt processible. It can comprise, for example, a powder, a metallic material, or a thermoset material. The substance 30 can be in the form of a film or nonwoven web comprising thereon (or therein) a dry soap powder, adhesive, perfume, insect repellent, and the like. For example, substance 30 can be in the form of a pre-moistened wipe substrate, processed as a web into the substance delivery system of the present invention.

Each bond site 50 forms localized melt weakened portions in the region of the bond site such that upon application of a force having a vector component parallel to the respective transverse axis t, sufficient to cause the bond site 50 to fracture, or tear, or otherwise fail in tension, an aperture, or opening, is formed in substance delivery system 10. The vector component of the applied force must be sufficient to fracture the melt weakened region of bond site 50, and, therefore, the force required can be minimized, for a given combination of webs and substances, by applying the force wholly parallel to transverse axis t. In one embodiment, this is accomplished by a user grasping a substance delivery system 10 along the appropriate opposing edges and pulling, such that the system can be considered to be a two-dimensional system, with substantially all the forces applied in a direction corresponding to the transverse axis t of a respective bond site. In another embodiment, the applied force can be generated by the usage regimen in which the user initiates a process that indirectly applies sufficient tensioning forces. Therefore, with respect to vector components of applied forces, the term "parallel to the transverse axis" is meant to distinguish forces that may be applied, for example, in what is denoted as the "Z" direction in FIG. 6. The relatively high aspect ratio of melt bond sites 50, permits relatively large apertures to be formed upon sufficient extension.

Figure 7:
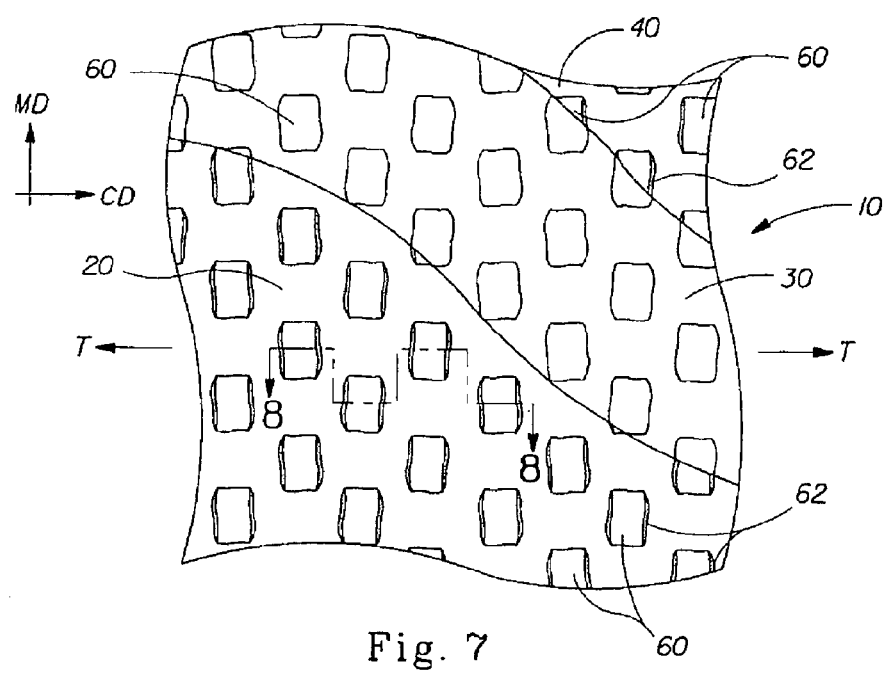
FIG. 7 is a cross-sectional view of a portion of the laminate web shown in FIG. 5 after user activation.
Figure 8:
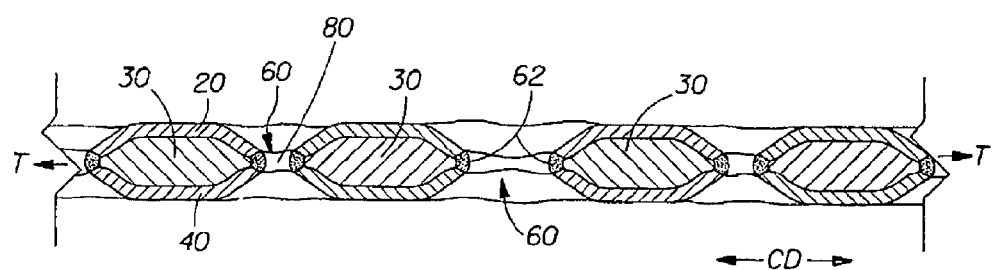
FIG. 8 is a cross-sectional view of a portion of the laminate web shown in FIG. 7.

With reference to FIGS. 5–8, if at least one bond site 50 is oriented with its respective longitudinal axes l aligned in the machine direction MD, and tension is applied in the direction T corresponding to the cross-direction CD, the tensile force applied at the bond site 50 will cause the bond site to rupture, open and spread, forming an aperture, or opening 60 as shown in FIGS. 7 and 8. In general, for a plurality of bond sites 50, when the substance delivery system 10 is uniformly tensioned, the result is a regular pattern of a plurality of apertures 60 corresponding to the pattern of bond sites 50. The requisite force application can be applied by a user by simply grasping the substance delivery system 1 by the appropriate edges and pulling with sufficient force to effect fracture and opening of the bond site(s) 5.

FIG. 7 shows a partially cut-away representation of a substance delivery system 10 of the present invention. As shown, the partial cut-away permits each layer or ply to be viewed in a plan view. The substance delivery system 10 shown in FIG. 7 is shown after being stretched by the user in the appropriate direction, as described above, with respect to the longitudinal axes, l, of the bond sites, 50, in this case, in the cross-machine direction, CD with sufficient elongation in the direction of extension to cause apertures to form. As shown, where formerly were bond sites 50, apertures 60 are produced as the relatively weak bond sites fail in tension.

When apertures 60 are formed, the thermally bonded portions of outer layers 20 and 40 remain primarily on the portions of the aperture perimeters corresponding to the length dimension of bond sites 50. Therefore, each aperture 60 does not have a full perimeter of thermally bonded material, but only portions remain bonded, represented as 62 in FIG. 7. The unbonded portions of the perimeter of each aperture facilitate fluid communication with the interior region 80. Once fluid communication with interior region 80 is achieved, substance exposure or delivery can be accomplished. For example, liquid substance 30 can be delivered, such as by being expressed, out of the substance delivery system 10.

In one embodiment, perfume can be supplied as substance 30 in a system comprising fluid impervious film outer layers 20 and 40. Once activated by the user, fluid communication with interior region 80 is facilitated, and the perfume can be released, or delivered to the user. Likewise, if the substance 30 is dry, powdered soap, for example, the aforementioned fluid communication facilitates contact between the soap and water. Upon contact with water, the soap can lather and is useful washing one's skin, for example.

FIG. 8 is a schematic representation of the cross-section denoted in FIG. 7. As shown, apertures 60 form when the system 10 is elongated in the direction T. The rectangular shaped apertures 60 shown as in FIG. 7 are known to occur when outer layers 20 and 40 comprise nonwoven web materials, in which significant separation and extension of the constituent fibers can occur about the perimeter of apertures 60. However, other shapes can occur, depending on the constituent materials utilized.

For substance delivery system 10, substance 30 can be any of a great number of various substances, in various forms. For example, depending on the particular selection of outer layers 20 and 40 (i.e., whether or not liquid permeable) substance 30 can be liquid, such as water, water-based cleansers, alcohol, antibacterial lotions, oil-based lotions, perfume, insect repellent, paint, or nail polish remover, for example. Likewise, substance 30 can comprise more viscous substances, such as creams, toothpaste, petrolatum, wax, or adhesives, for example. Furthermore, substance 30 can be delivered on, or as a constituent member of, tissue paper, thermoplastic film, metal foil, closed or open cell foam, or any other material that can be processed by the method described herein. In general, all relatively low basis weight paper webs, tissue paper webs, nonwoven webs, thin films (including metallic foils), and thin foam materials can be processed as described herein.

Other variations of the present invention can be achieved by utilizing additional layers, or plies, of materials to form substance delivery systems 1 having multiple void spaces 8 or interior regions 80. For example, as shown in cross section in FIGS. 13–15, the substance delivery system 1 can comprise a plurality of distinct void spaces 8 and/or interior regions 80. Thus, for example, as shown in FIGS. 13 and 14, the substance delivery system 1 can facilitate exposure and delivery of two-part compositions, such as dye and bleach compositions (for hair care applications, for example), or epoxy compositions having A and B parts.

Figure 13:
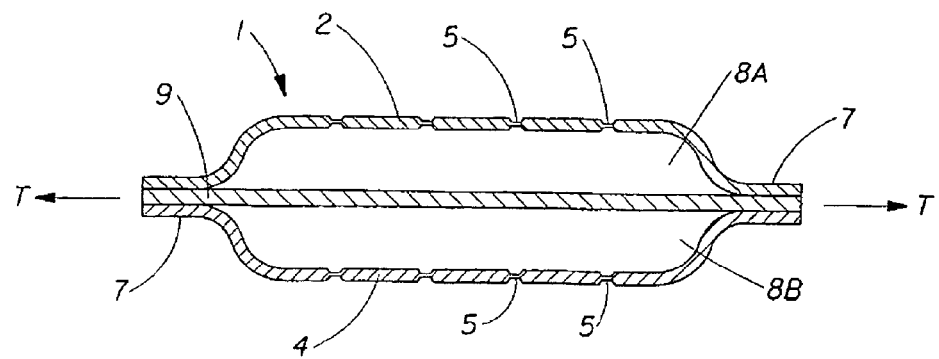
FIG. 13 is a cross-sectional view of another embodiment of the present invention.

As shown in FIG. 13, a two-compartment embodiment of the present invention can comprise outer layers 2 and 4 as described above. However, laminated between the two outer layers is an unapertured, fluid impervious layer 9 that serves to separate the void spaces 8A and 8B. In this manner, a first substance 30 can be disposed in void space 8A, and a different, second substance 30 can be disposed in void space 8B. In this manner, upon activation to fracture bond sites 5, the substance are exposed on their respective sides of the substance delivery system, and can be utilized accordingly. For example, the first substance could be a solvent, and the second substance could be a cleaning fluid, for cleaning glass windows.

Figure 14:
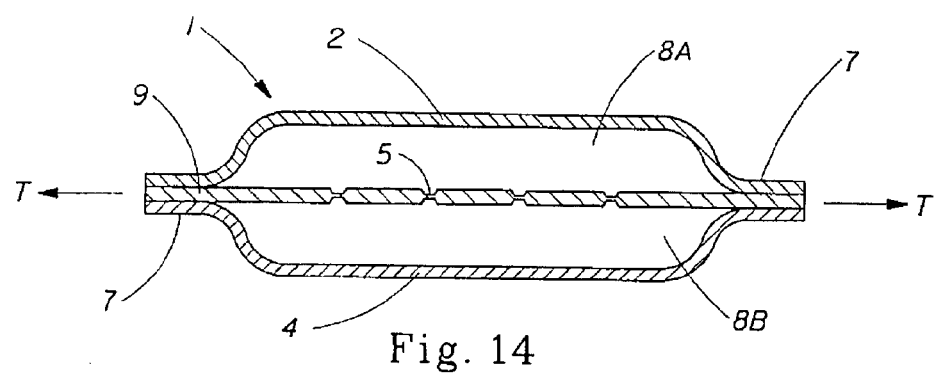
FIG. 14 is a cross-sectional view of another embodiment of the present invention.

As shown in FIG. 14, a two-compartment embodiment of the present invention can comprise outer layers 2 and 4 that may or may not have bond sites that rupture upon application of tensile forces. (As shown in FIG. 14, the outer layers 2 and 4 do not have bond sites.) However, laminated between the two outer layers is an unapertured, fluid impervious layer 9 that serves to separate the void spaces 8A and 8B. Layer 9 has at least one bond site 5, such that upon sufficient tensioning in the direction T, as indicated, bond sites 5 fail, forming apertures, and facilitating fluid communication between void space 8A and 8B. In this manner, a first substance 30 can be disposed in void space 8A, and a different, second substance 30 can be disposed in void space 8B such that, upon activation to fracture bond sites 5, the first and second substances can be mixed, such as by massaging the still-unapertured outer layers. For example, the first substance could be part A of a two-pan epoxy, and the second substance could be part B. Upon sufficient mixing after activation, the substance delivery system 1 can be opened by methods known in the art to dispense the mixed epoxy.

Figure 15:
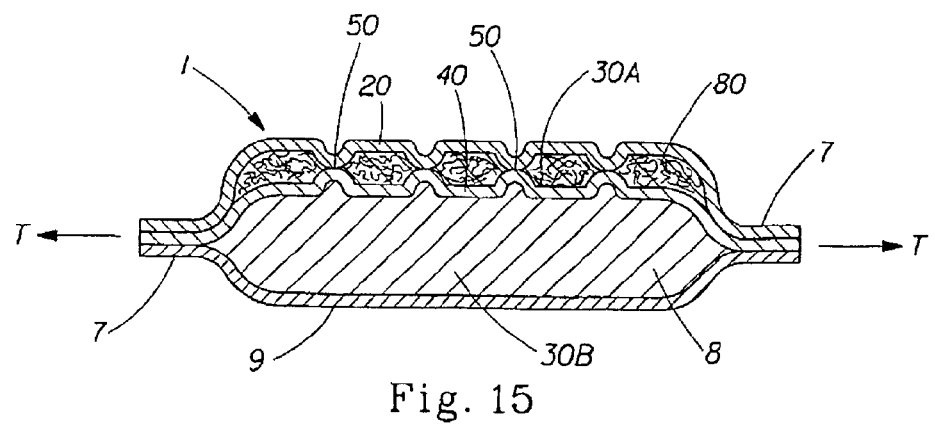
FIG. 15 is a cross-sectional view of another embodiment of the present invention.
Figure 16A:
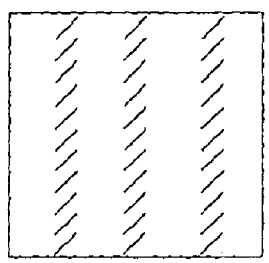
FIGS. 16 A–I are representative patterns of bond site patterns according to the present invention.
Figure 16B:
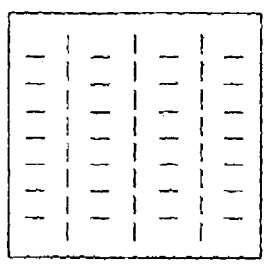
Figure 16C:
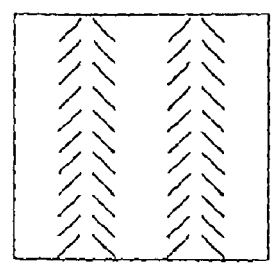
Figure 16D:
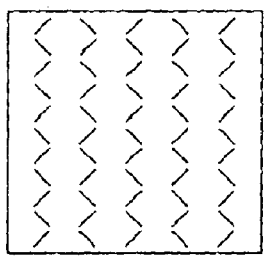
Figure 16E:
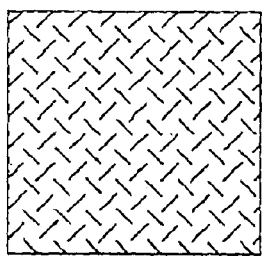
Figure 16F:
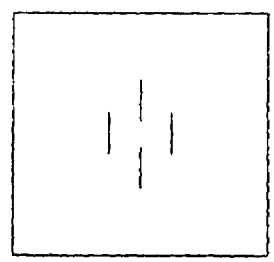
Figure 16G:
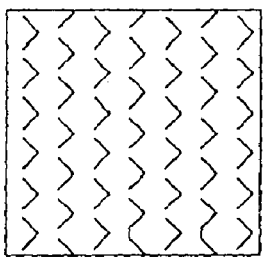
Figure 16H:
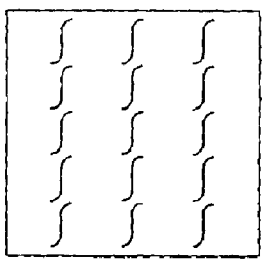
Figure 16I:
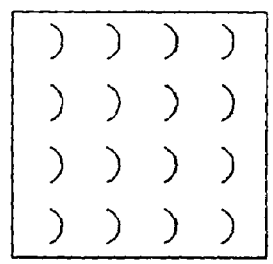

In the embodiment shown in FIG. 15, substance delivery system 1 can comprise layers 20 and 40 defining interior regions 80, in addition to a third layer 9 defining a void space 8. For example, layers 20 and 40 can be thermoplastic films enclosing a relatively low viscosity fluid 30A within the interior region 80. Layer 9 can be a nonwoven film, such that when extended in the direction the direction T, the fluid is released from the interior region and at least partially into the void space 8. The fluid can then contact and saturate the nonwoven layer 9, which then can be used as a soft, pliable, application surface. Alternatively, layer 20 can be a nonwoven layer, and layer 40 can be an impervious film layer, layers 20 and 40 defining an interior region 80 enclosing a dry, absorbent substance 30A. Layer 9 can be an impervious film, together with layer 40 defining a void space 8 enclosing a fluid substance 30B. When activated by stretching in the direction T, bond sites 50 fracture, causing fluid communication to occur between interior region 80 and void space 8. Such an article can be used a cleaning cloth, with the absorbent substance 30A serving to hold cleaning fluid, and absorb soiled fluid.

Method of Making

Figure 9:
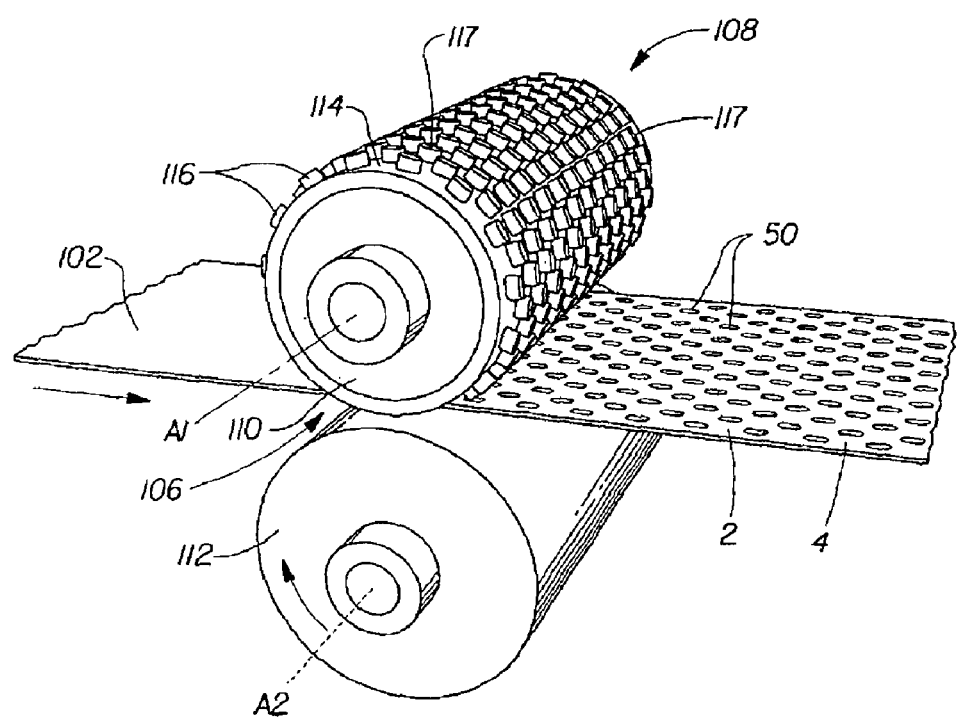
FIG. 9 is a perspective view of a melt bond calendaring apparatus.

Referring to FIG. 9 there is schematically illustrated a thermal point bond roller arrangement 108 for forming bond sites 5. Web 102 represents a film, a nonwoven, or a laminate comprising more one or more films or one or more nonwovens, and combinations thereof, useful for the embodiment shown in FIG. 1. Therefore, shown schematically as a single web, the process works the same for multiple webs processed as a laminate. If web 102 comprises a nonwoven web, it can be made by any of the known methods, and can have a basis weight between about 10 to about 100 gsm, and can be from about 15 to about 30 gsm. Likewise if web 102 comprises a film, such as a thermoplastic film, it can be made of known materials, by known methods, and can have a basis weight between about 10 and 250 gsm, more preferably about 10 to 40 gsm. Web 102 is preferably delivered from roll stock and processed in the direction indicated by the arrows associated therewith to pass through a nip 106 formed by the juxtaposition of rollers 110 and 112.

Referring to FIG. 9, the thermal bond roller arrangement 108 comprises a patterned calendar roller 110 and a smooth anvil roller 112, each of which rotates about parallel axes A1 and A2, respectively. One or both of the patterned calendar roller 110 and the smooth anvil roller 112 can be heated and the temperature of either roller and the pressure between the two rollers may be adjusted by well known means to provide the desired temperature and pressure to form a plurality of bond sites 5. In certain embodiments, the required temperature to achieve thermal bonding can be effected via pressure and friction between the calendar rollers. However, at least one heated roller is preferred for commercially viable processing.

Other particulars of the patterned calendar roller 110 are described more fully below with respect to the full processing apparatus 100. In general, however, it is mentioned here that calendar roller 110 is configured to have a circular cylindrical surface 114, and a plurality of protuberances or pattern elements 116 which extend outwardly from surface 114 and each have a distal end surface 117 having a high aspect ratio corresponding to the aspect ratio disclosed above with respect to bond sites 5. Although it is not intended to thereby limit the scope of the present invention to protuberances of only this configuration, it is currently believed that the high aspect ratio of the bond site 5 is only achievable if the protuberances likewise have a narrow width and a high aspect ratio at the distal end surfaces 117.

Once the web 102 is processed through the thermal bond roller arrangement 108 to have bond sites 5 it is suitable for further processing into either outer layer 2 or 4 as described above for substance delivery system 1. Processing can be by any means known in the art for forming such packages, including pouches. For example, a nonwoven or film web material having bond sites 5 can be cut to a selected size and shape to form layer 2 or 4, the substance 3 can be placed such that it is disposed between the layers 2 and 4, and the edges of the layers 2 and 4 can then be sealed, for example by suitable adhesive or by thermal bonding.

The substance delivery system 1 of the present invention can be modified as desired. For example, it may be desirable to have only one of layers 2 or 4 capable of forming apertures upon extension by the user to activate. That is, only one of either layer 2 or 4 would have bond sites 5 which, upon extension by the user, would fracture and extend to form apertures 6. In such an embodiment, it is preferred that the other layer, 2 or 4 have sufficient extensibility so as not to unduly hinder the extension of the system 1. Of course, in such an embodiment, the layer that does not have bond sites 5 can be chosen for the primary purpose of governing the amount of force necessary to be exerted by the user to effect sufficient extension for the formation of apertures 6. Further, either layer 2 or 4 can be configured so as to limit the amount of total extension that can be reasonably induced by a user. For example, either layer 2 or 4 may exhibit a two-stage force-elongation behavior as taught in U.S. Pat. No. 5,518,801 issued to Chappell et al., herein incorporated by reference in its entirety.

Figure 10:
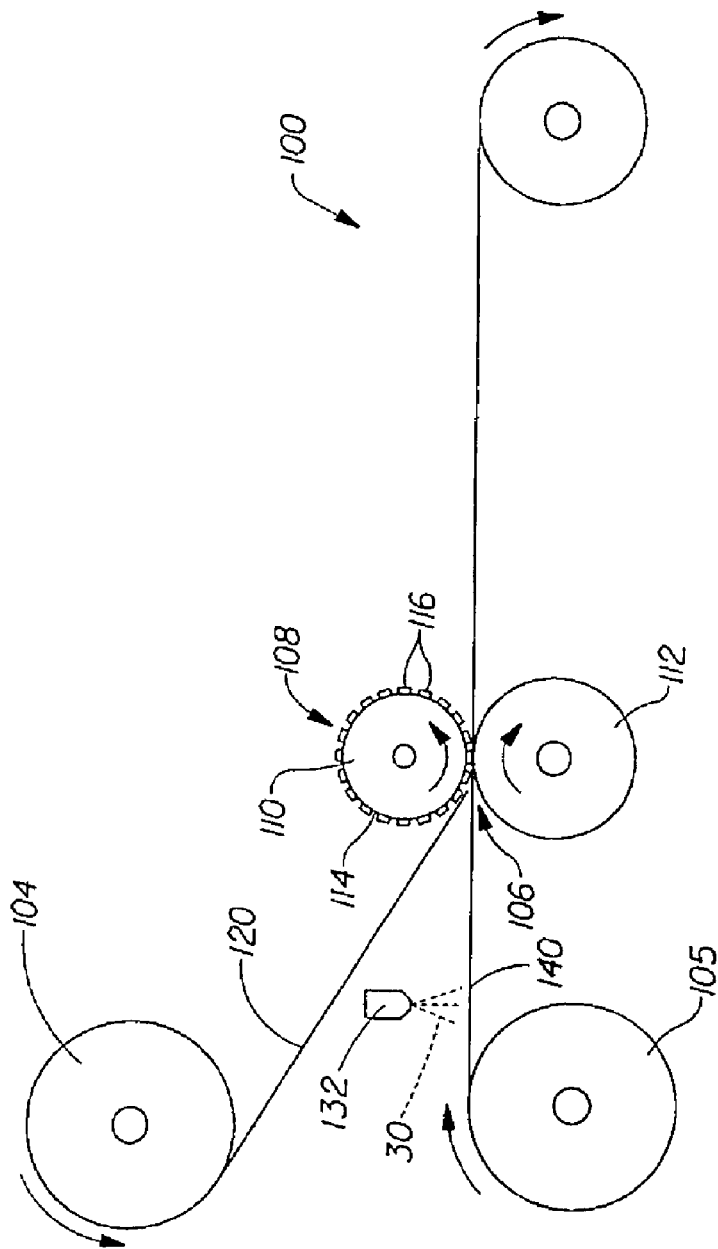
FIG. 10 is a schematic representation of a process for making a user-activatible substance delivery system of the present invention.

With reference to FIG. 10, there is schematically illustrated at 100 a process making a substance delivery system 10 of the present invention.

A first web 120 is unwound from a supply roll 104 and travels in a direction indicated by the arrows associated therewith as the supply roll 104 rotates in the direction indicated by the arrows associated therewith. Likewise a second web 140 is unwound from supply roll 105. A substance 30, which can be any of the substance disclosed hereinabove, is deposited upon web 140 (or 120) so as to ultimately be contained between webs 120 and 140, by any suitable means. For example, if substance 30 is a powdered substance, it could be deposited from a suitable feedbox by gravity feed, or assisted gravity feed. If substance 30 is a liquid it could be applied by spraying, or by wiping, rolling, or otherwise depositing the liquid on web 140. If substance 30 is a viscous substance, it could be applied by extrusion, for example. The non-limiting example shown in FIG. 10 shows a sprayer apparatus 132 spraying a liquid substance 30 onto web 140. Of course, if large amounts of a liquid substance must be deposited, suitable processing parameters as known in the art can be employed. For example, the lateral edges of web 140 could be guided upwardly such that web 140 forms a shallow trough into which substance 30 is deposited. At the thermal point bonding apparatus 108, the lateral edges of the webs could be bonded in a known manner to capture the substance 30 in the interior regions 80.

Either outer layer web material 120 or 140 can comprise thermofusable nonwoven materials, such as thermoplastic nonwoven materials or a polymeric film, for example a polyolefinic (e.g., PP or PE) thin film. If the entire outer layer is not uniformly thermofusable, at least sufficient amounts to effect melt bonding at bond sites 50 must be thermofusable. Conjugate fibers, such as bicomponent fibers, with configurations of, for example, sheath-core, side-by-side, islands-in-the-sea, and segmented pies, can be used in the outer layers to facilitate thermal bonding of the outer layers. Either outer layer can comprise a formed film, such as a three-dimensional formed film having micro-apertures such as described in commonly-assigned U.S. Pat. No. 4,629,643 issued to Curro et al. on Dec. 16, 1986, and U.S. Pat No. 4,609,518, issued to Curro et al. on Sep. 2, 1986.

In one embodiment, both webs 120 and 140 comprise nonwoven materials, and which may be identical. The nonwoven material may be formed by known nonwoven extrusion processes, such as, for example, known meltblowing processes or known spunbonding processes, and passed directly through the nip 106 without first being bonded and/or stored on a supply roll. However, in a preferred embodiment, the nonwoven webs are themselves thermally point bonded (consolidated) webs commercially available on supply rolls. The thermal point bonds, which are typically in the form of a regular pattern of spaced-apart bond sites, are present in the nonwoven as purchased from a nonwoven vendor, and are to be distinguished in the web of the present invention from the bond sites 50 having a high aspect ratio formed by the method of the present invention, as discussed above.

Outer layer(s) 120 and 140 may be elastic, highly elastic or nonelastic. The nonwoven web may be any thermofusable web, including a spunbonded web, a meltblown web, or a bonded carded web. If the nonwoven web is a web of meltblown fibers, it may include meltblown microfibers. The nonwoven web may be made of fiber forming polymers such as, for example, polyolefins. Exemplary polyolefins include one or more of polypropylene, polyethylene, ethylene copolymers, propylene copolymers, and butene copolymers. The nonwoven web can have a basis weight between about 10 to about 100 gsm, and more preferably about 15 to about 30 gsm.

The outer layers may themselves be a multilayer material having, for example, at least one layer of a spunbonded web joined to at least one layer of a meltblown web, a bonded carded web, or other suitable material. For example, the nonwoven web may be a multilayer web, such as an SMS nonwoven, having a first layer of spunbonded polypropylene having a basis weight from about 3 gsm about 8 gsm, a layer of meltblown polypropylene having a basis weight from about 3 gsm to about 8 gsm, and a second layer of spunbonded polypropylene having a basis weight from about 3 gsm to about 8 gsm. The nonwoven web outer layers may also be a composite made up of a mixture of two or more different fibers or a mixture of fibers and particles. Such mixtures may be formed by adding fibers and/or particulates to the gas stream in which meltblown fibers or spunbond fibers are carried so that an intimate entangled co-mingling of fibers and other materials, e.g., wood pulp, staple fibers and particles occurs prior to collection of the fibers.

Figure 12:
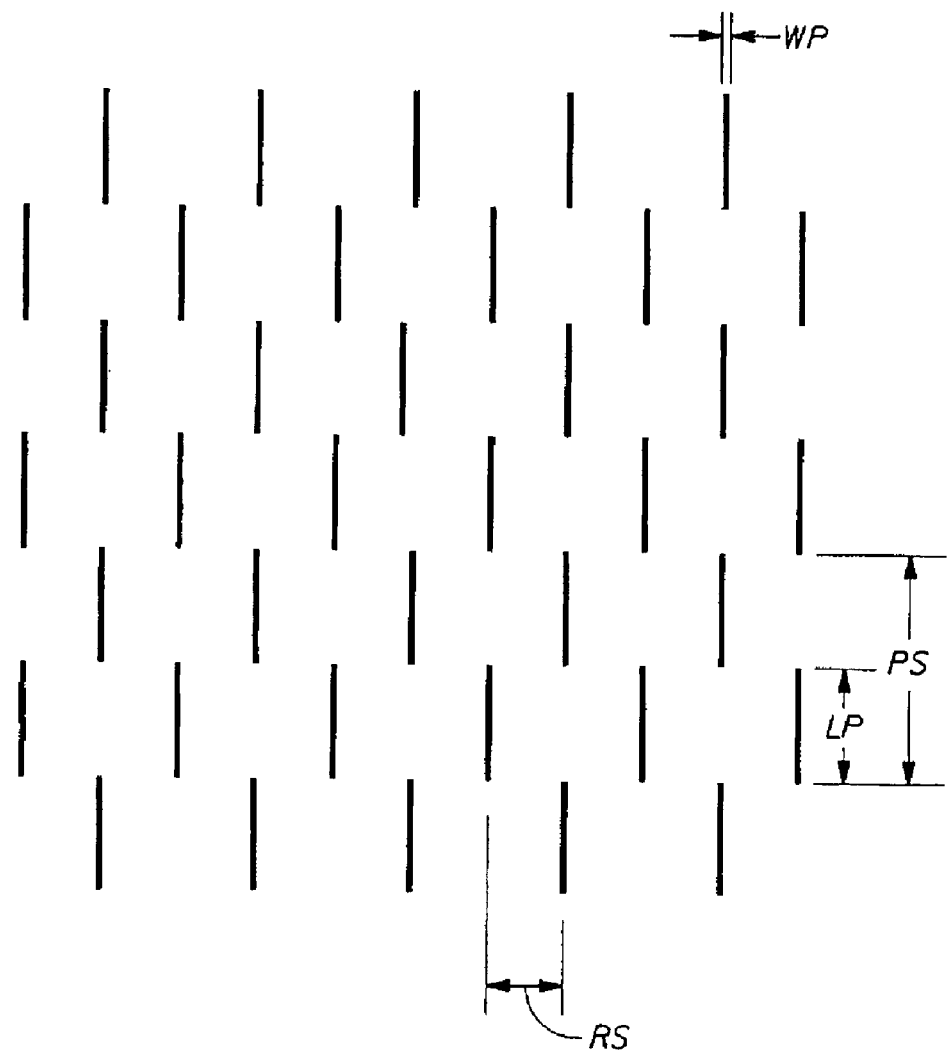
FIG. 12 is a schematic representation of a pattern for the protuberances of the calendaring roll.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to displace substance 30 at melt bond sites, and melt bond the two outer layers together at a plurality of locations. One pattern of protuberances is shown schematically in FIG. 12. As shown, the protuberances 116 have a relatively small width, WP, which can be between about 0.003 inches and 0.020 inches, but in a preferred embodiment is about 0.010 inches. Protuberances can have a length, LP, of between about 0.030 inches and about 0.200 inches, and in a preferred embodiment has a length of about 0.100 inches. In a preferred embodiment, the protuberances have an aspect ratio (LP/WP) of 10. The pattern shown is a regular repeating pattern of staggered protuberances, generally in rows, each separated by a row spacing, RS, of about between about 0.010 inches and about 0.200 inches. In one embodiment, row spacing RS is about 0.060 inches. The protuberances can be spaced apart within a row by protuberance spacing, PS generally equal to the protuberance length, LP. But the spacing and pattern can be varied in any way depending on the end product desired, such as the area coverage of exposure or release, initial rate of release, and aesthetic qualities.

As shown in FIG. 9, patterned calendar roller 110 can have a repeating pattern of protuberances 116 which extend about the entire circumference of surface 114. Alternatively, the protuberances 116 may extend around a portion, or portions of the circumference of surface 114. Likewise, the protuberances 116 may be in a non-repeating pattern, or in a repeating pattern of pseudo-randomly oriented protuberances. The protuberances 116 are preferably truncated conical shapes which extend radially outwardly from surface 114 and which have rectangular or somewhat elliptical distal end surfaces 117. Although it is not intended to thereby limit the scope of the present invention to protuberances of only this configuration, it is currently believed that the high aspect ratio of the bond site 50 is only achievable if the protuberances likewise have a narrow width and a high aspect ratio at the distal end surfaces 117, as shown above with reference to FIG. 11. The roller 110 is preferably finished so that all of the end surfaces 117 lie in an imaginary right circular cylinder that is coaxial with respect to the axis of rotation of roller 110.

The height of the protuberances should be selected according to the thickness of the materials being bonded. In general, the height dimension should be greater than the maximum thickness of the layered materials being bonded during the calendaring process, so that adequate bonding occurs at the bond sites, and only at the bond sites. However, the thickness of the materials entering nip 106 can be greater than the height of the protuberances as long as bond sites 50 are still maintained.

Anvil roller 112, is preferably a smooth surfaced, right circular cylinder of steel.

After passing through nip 106, the two outer webs 120 and 140 have been bonded together to form a unitary substance delivery system 10. At this point in the process the outer layers are thermally bonded to each other and unapertured, as shown in FIGS. 5 and 6. Substance(s) 30 has been substantially displaced by protuberances 116 in nip 106. Depending on the substance(s) used, it (they) may or may not fully participate in the bonding about the periphery of the bond sites 50. In preferred embodiments, the substance delivery system 10 can be cut to desired size and shape, and further finished with appropriate edge sealing, further packaging, or other processing steps as required for a particular finished product. Additionally, individual processed substance delivery systems 10 can be packaged together for bulk sale to consumers. For example, multiple units of individual substance delivery systems 10 can be packaged in bulk, and dispensed individually by the consumer.

Figure 11:
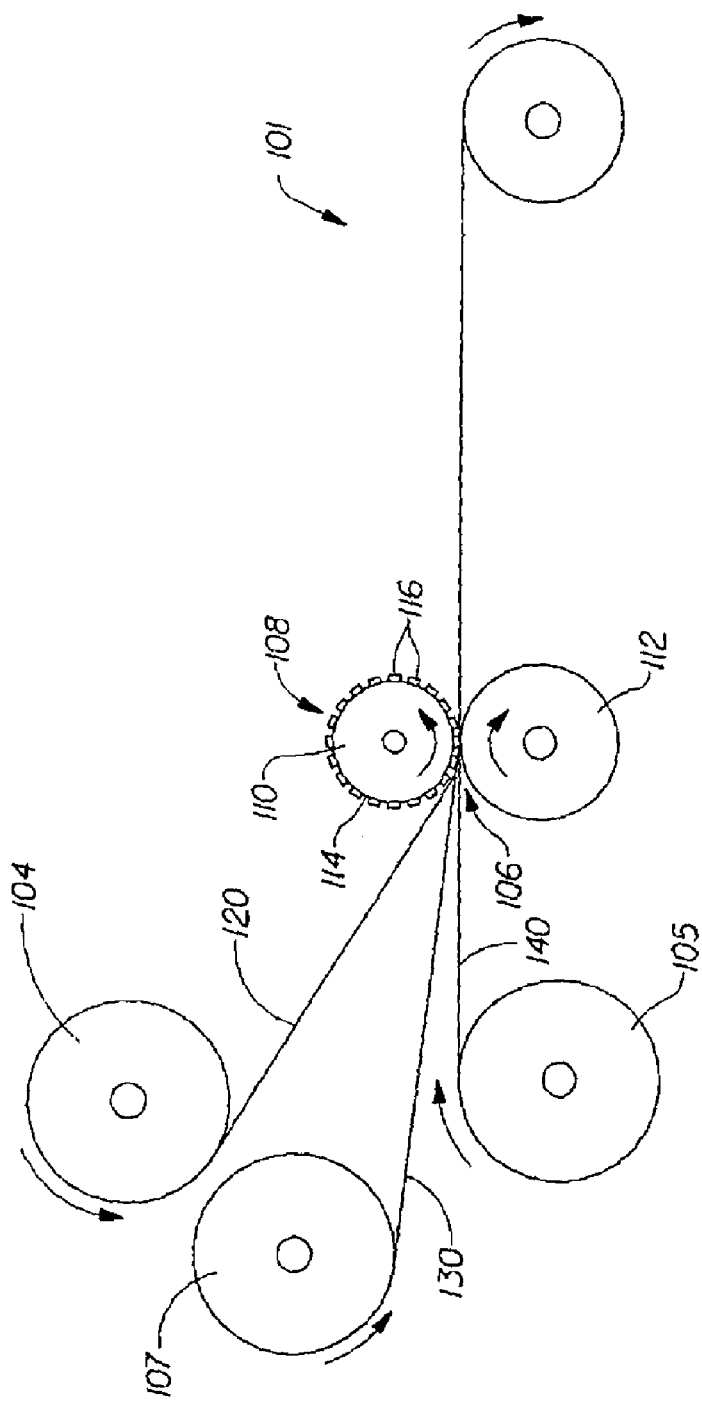
FIG. 11 is a schematic representation of another process for making a user-activatible substance delivery system of the present invention.

A further embodiment of substance delivery system 10 can be produced by the modified process 101 schematically represented in FIG. 11. The process 101 is essentially identical to process 100 described above, except that substance 30 is supplied as, or on, or in, web 130. Web 130 is supplied as roll stock from roll 107 and fed in the direction shown into nip 106 and processed as shown above. For example, web 130 may be a pre-moistened nonwoven web, having a specified moisture content comprising an aqueous cleansing solution substance 30. Thus, substance 30 is in web 130, and can be expressed out through apertures 60 after activation of substance delivery system 10, as described above.

Additionally, in another embodiment, web 130 may be a fluid impervious film having a powdered, dry soap substance 30 disposed on one side thereof. In this embodiment, the substance delivery system can be "sided", that is, the properties can be different, depending on which side is considered. As shown in FIG. 11, for example, if a dry, powdered soap were disposed as substance 30 on the side of web 130 facing web 120, then in the finished product, all, or most of soap substance 30 would be delivered on the side of substance delivery system 10 associated with layer 20. This can be beneficial for applications in which the user desires to have soap substance 30 for cleaning, and a relatively soap-free substance 30 for rinsing, all delivered in the same article.

While particular embodiments of the present invention have been illustrated and described, it would be obvious to those skilled in the art that various other changes and modifications can be made without departing from the scope of the invention. For example, FIGS. 16 A–I show various bond site 5, 50 configurations possible, without departing form the scope of the invention. These are meant to be representative and non-limiting, with the point being that any number of variations of bond site patterns can be usefully employed in the present invention. In particular, attention is drawn to FIGS. 16 G–I in which the bond sites are non-linear. Such a bond site results in a very beneficial three-dimensional puckering of the delivery system upon sufficient extension as described herein. It is therefore intended to cover in the appended claims all such changes and modifications that are within the scope of this invention.

What is claimed is:

1. A user-activatible substance delivery system:
    (a) a first web and a second web, said first web joined to said second web in a face to face relationship at least one discrete bond site and said first and second webs having a periphery and being joined about their respective peripheries and defining a void space therein;
    (b) a substance disposed in said void space, wherein said substance comprises a fluid;
    (c) said bond site having a longitudinal axis oriented in a first direction and a transverse axis oriented in a second direction orthogonal to said first direction; and
    (d) said bond site defining a melt weakened region having an aspect ratio of at least about 3, such that upon application of a sufficient force having a vector component parallel to said transverse axis, said bond site fractures to form a corresponding aperture to facilitate exposure of said substance.

2. The user-activatible substance delivery system of claim 1, wherein said first or second web comprises a nonwoven.

3. The user-activatible substance delivery system of claim 1, wherein said first or second web comprises a polymeric film.

4. The user-activatible substance delivery system of claim 1, wherein said first and second webs are identical.

5. The user-activatible substance delivery system of claim 1, wherein said fluid substance comprises a relatively viscous fluid.

6. The user-activatible substance delivery system of claim 1, wherein said bond site has a width of less than about 0.020 inches.

7. A user-activatible substance delivery system:
    (a) a first web, a second web, and a third web, said first second and third webs having a periphery and being joined about their respective peripheries and defining two void spaces therein;
    (b) a substance disposed in each of said void spaces;
    (c) at least one of said first, second, or third webs having a least one bond site, said bond site having a longitudinal axis oriented in a first direction arid a transverse axis oriented in a second direction orthogonal to said first direction; and
    (d) said at least one bond site defining a melt weakened region having an aspect ratio of at least about 3, such that upon application of a force having a vector component parallel to said second direction, said at least one bond site fractures to form a corresponding aperture to facilitate exposure of said substance.

8. The user-activatible substance delivery system of claim 7, wherein each of said first and second webs comprise at lease one bond site.

9. The user-activatible substance delivery system of claim 7, wherein said substance comprises a fluid.

10. The user-activatible substance delivery system of claim 9, wherein said fluid substance comprises a liquid.

11. The user-activatible substance delivery system of claim 9, wherein said fluid substance comprises a relatively viscous material.

12. The user-activatible substance delivery system of claim 7, wherein said substance comprises a powdered material.

13. The user-activatible substance delivery system of claim 7, wherein said bond site has a width of less than about 0.020 inches.

14. A user-activatible substance delivery system comprising:
    (a) a first web;
    (b) a second web joined to said first web in a face to face relationship at a plurality of discrete bond sites, at least a first portion of said bond sites each having a longitudinal axis oriented in a first direction and a transverse axis oriented in a second direction orthogonal to said first direction.
    (c) said first and second webs defining an interior region and an exterior region; and
    (d) a fluid or powdered substance being disposed between said first and second webs, said substance capable of being exposed to said exterior via a plurality of apertures formed by the fracture of said bond sites upon sufficient application of a force having a vector component parallel to said second direction.

15. The user-activatible substance delivery system of claim 14, wherein said first or second web comprises a film/nonwoven laminate material.

16. The user-activatible substance delivery system of claim 14, wherein said fluid substance comprises a liquid.

17. The user-activatible substance delivery system of claim 14, wherein said fluid substance comprises a relatively viscous fluid.

18. The user-activatible substance delivery system of claim 14, wherein said substance comprises a cleansing powder.

19. The user-activatible substance delivery system of claim 14, wherein bond site has a width of less than about 0.020 inches.

20. The user-activatible substance delivery system of claim 14, wherein said bond site has an aspect ratio of greater than about 3.

* * * * *

UNITED STATES PATENT AND TRADEMARK OFFICE
CERTIFICATE OF CORRECTION

PATENT NO. : 6,863,960 B2
DATED : March 8, 2005
INVENTOR(S) : Curro et al.

It is certified that error appears in the above-identified patent and that said Letters Patent is hereby corrected as shown below:

Column 15,
Line 6, "two pan" should be -- two-part --

Signed and Sealed this

Seventh Day of June, 2005

JON W. DUDAS
*Director of the United States Patent and Trademark Office*